United States Patent [19]

Steigmeier et al.

[11] 4,391,524
[45] Jul. 5, 1983

[54] METHOD FOR DETERMINING THE QUALITY OF LIGHT SCATTERING MATERIAL

[75] Inventors: Edgar F. Steigmeier, Hedingen; Heinrich Auderset, Horgen, both of Switzerland

[73] Assignee: RCA Corporation, New York, N.Y.

[21] Appl. No.: 244,060

[22] Filed: Mar. 16, 1981

[51] Int. Cl.³ ........................................... G01N 21/01
[52] U.S. Cl. ...................................... 356/338; 356/237
[58] Field of Search ................................ 356/445–448, 356/338, 342, 430, 431, 237

[56] References Cited

U.S. PATENT DOCUMENTS 4,314,763 2/1982 Steigmeier et al. .................. 356/237
4,352,016 9/1982 Duffy et al. ....................... 250/358.1
4,352,017 9/1982 Duffy et al. ....................... 250/358.1

Primary Examiner—Bruce Y. Arnold
Attorney, Agent, or Firm—Birgit E. Morris; Donald S. Cohen; Joseph D. Lazar

[57] ABSTRACT

A method of determining the crystalline quality of heteroepitaxial silicon material, particularly silicon-on-sapphire (SOS) and of homoepitaxial silicon material which uses the light scattering is disclosed. The material is exposed to a beam of light of a selected wavelength, and scattered light having an intensity above a threshold is detected to provide a signal which is used to control the intensity of a display beam of a visual display device. The threshold is varied to thereby vary the display beam intensity so as to provide the minimum intensity of display beam which yields a full display. The value of the thusly adjusted threshold intensity is used as a direct measure of the quality of the material.

12 Claims, 10 Drawing Figures

TAKEN AT THRESHOLD (I) SETTING 740

TAKEN AT THRESHOLD (I) SETTING 720

TAKEN AT THRESHOLD (I) SETTING 700

METHOD FOR DETERMINING THE QUALITY OF LIGHT SCATTERING MATERIAL

This invention is a method for determining the crystalline quality of light scattering material, and more particularly of silicon material epitaxially grown on sapphire or silicon substrates.

BACKGROUND OF THE INVENTION

Silicon wafers useful in the manufacture of semiconductor devices require close scrutiny to detect defects as soon as possible in the manufacturing process. Several apparatus are known in the art for detecting microscopic defects on the surface or near the surface of such devices. One such apparatus utilizes a laser beam that is scanned over the surface of a wafer and includes means for detecting scattered radiation from the wafer surface. The specular reflection is blocked from the detection device by suitable arrangement of the lenses and spatial filters. If the surface of the wafer has an imperfection such as dirt, hills, scratches and the like, the laser beam will be scattered from the imperfection. There are also scattering processes such as Raman scattering, etc., which occur, but the intensity of the light due to such scattering effects is usually negligible. The scattered light from the wafer is collected from about the main axis of the lens and is focused on a detector. The scattered light is converted to electrical impulses which can be counted or, in the alternative, can be displayed as a bright spot on an oscilloscope or other monitor. See copending U.S. application Ser. No. 000,813, filed by E. F. Steigmeier et al. on Jan. 4, 1979 now U.S. Pat. No. 4,314,763, issued Feb. 9, 1982 entitled "DEFECT DETECTION SYSTEM" for a detailed description of such a scanning apparatus.

The use of such light scattering apparatus for detecting surface and subsurface defects by conventional light scanning techniques does not identify or test for the crystalline quality of the semiconductor material. The quality of such material is related to the purity or perfection of the crystallographic growth of the material on an atomic or microscopic scale. Deviations from the ideal crystallographic perfection can be said to be a reduction in the quality of the material. The better the quality the closer the material is to the ideal crystallographic perfection. The term "crystallographic quality" includes structural conditions known to more or less extent in the art. For example, "mosaic spread" can be a deviation from the ideal crystallographic structure caused by slight misorientation of the crystalline axis directions or mosaic spread can be manifested by larger misorientations of one area of the material against the adjacent area. Such larger misorientations might be called "grain" or "twinning." Other structural deviations of the crystalline structure of a semiconductor material are continuously being identified and analyzed in the art. However defined, the quality of the crystalline structure, it should be understood, is distinguished from the defects on the surface of the semiconductor material in the form of scratches, recesses, particulates, and the like.

In copending U.S. patent applications Ser. No. 189,348, filed on Sept. 22, 1980 and Ser. No. 189,356, filed on Sept. 22, 1980, now, respectively, U.S. Pat. Nos. 4,352,016 and 4,352,017, issued Sept. 28, 1982, both related to APPARATUS FOR DETERMINING THE QUALITY OF A SEMICONDUCTOR SURFACE, based on the inventions of M. T. Duffy, P. J. Zanzucchi, and J. F. Corboy, Jr., there is described a method and apparatus for determining the quality of the material of a semiconductor surface. In brief, the surface quality of the semiconductor material is determined by exposing the semiconductor surface to two light beams of different wavelengths or wavelength ranges (e.g., ultraviolet at 2,800 angstroms and near ultraviolet at 4,000 angstroms). A portion of each of the respective light beams is reflected from the semiconductor surface. The intensity of each reflected beam is measured to obtain an intensity difference whereby the magnitude of the difference is a measure of the quality of a semiconductor material. While the quality of semiconductor material can be tested or evaluated quite well using the ultraviolet two wavelength technique described in the above-identified Duffy, et al. patent applications, the time required to make such tests can be very long and not well suited for on-line evaluations needed in modern day semiconductor processing and manufacturing.

SUMMARY OF THE INVENTION

According to the present invention, a method using light scattering techniques provides a relative quality indication of wafers compared to each other or to a reference standard. The method comprises exposing the surface of a material to a wavelength of light sufficient to penetrate the bulk portion of the material to a depth of interest. To determine the crystalline quality of the material, the steps include detecting the scattered light, adjusting the threshold of intensity of the detected scattered light so that the display of the detected signal on a visual display is sufficient to provide a full display of the surface. The value of the threshold adjustment is a direct measurement of the crystalline quality of the material.

DETAILED DESCRIPTION OF A PREFERRED EMBODIMENT

Figure 1:
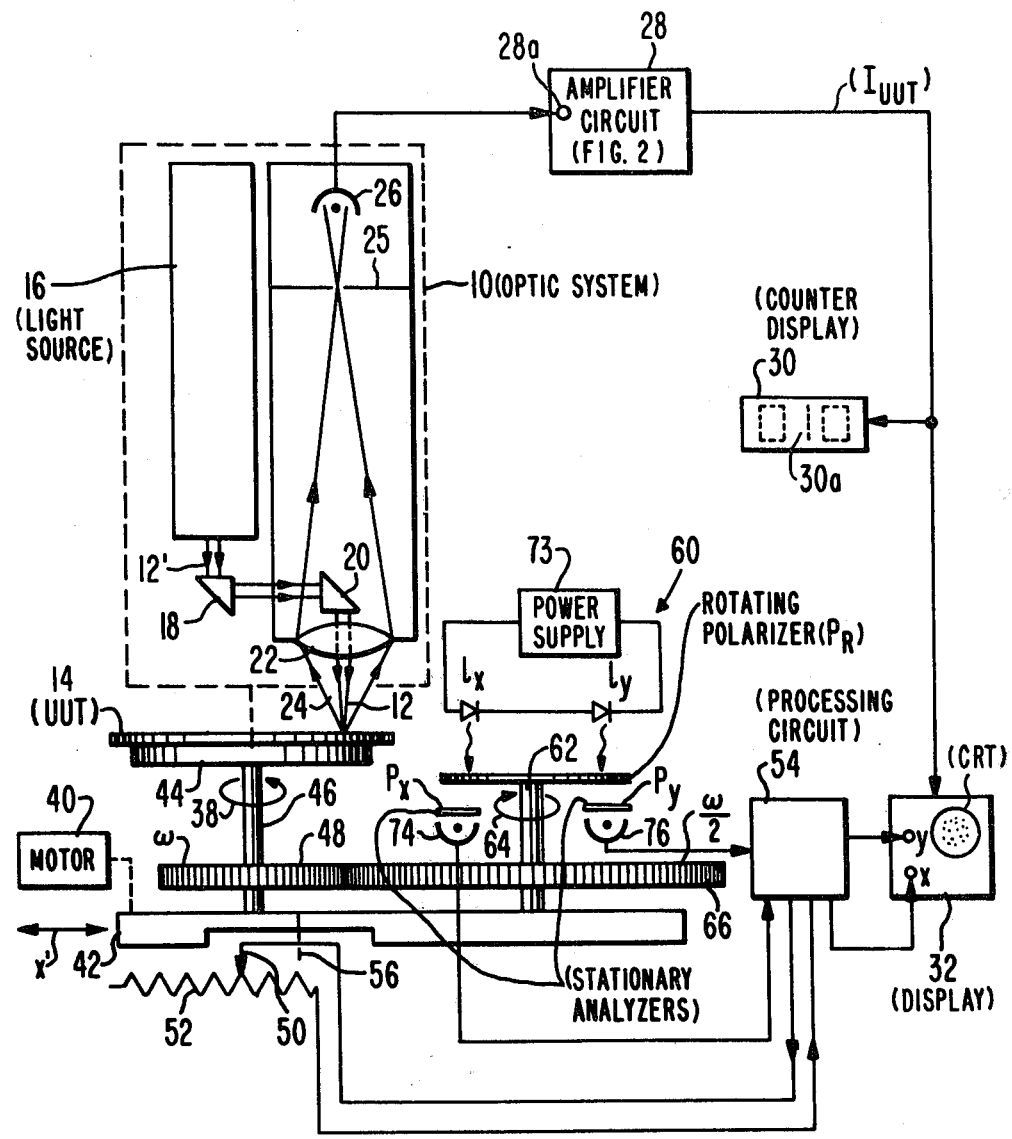
FIG. 1 is a schematic of an optical scanner apparatus useful in practicing the method of the present invention.

Before proceeding to a detailed description of the method of the invention of determining the quality of semiconductor material, reference is made to FIG. 1 illustrating a suitable optical scanner for which the method of the invention is used. The apparatus shown in FIG. 1 and described in detail in the above-identified Steigmeier et al. application, comprises an optical system 10 which includes a light source 16 providing a beam of light 12' passing through a series of prisms 18 and 20 and then through a focusing means such as lens 22 forming beam 12. The light source 16 provides a light of any selected wavelength and includes light in the infrared (IR), visible or ultraviolet (UV) light spectrum. Light source 16 may be a low power laser, for example, a HeNe laser producing light at 6323 angstroms in wavelength which is focused by lens 22 into a spot 250 μm in diameter. For optimized conditions (of minimum beam spot size) elliptical spot sizes of 40 μm by 250 μm may be produced by inserting an appropriate cylindrical/spherical lens system (not shown) in between the two prisms 18 and 20. Beam 12 of the laser light is projected onto the surface 14 of an object such as the unit under test (UUT). The unit under test may be a wafer of silicon as used in the manufacture of integrated circuits (IC) and other semiconductor devices. Preferably the UUT is a wafer of silicon on sapphire (SOS). However, wafers of epitaxial deposited silicon on substrates such as silicon, spinel, etc., may be used in the practice of this invention. Moreover, the quality of dielectric material and of amorphous silicon material may also be determined according to this invention.

The position of the light source 16 is not critical, but the position of the beam 12 between the prism 20 and object surface is important. The axis of the beam is preferably substantially perpendicular to the surface 14. Light generated by laser 16 is preferably scanned over the surface 14 of the UUT and is reflected back through the lens 22 via beam pattern 24 and collected on a photodetector 26 which is positioned along the axis of the beam 12. Lens 22 in combination with prism 20 serves as a first of two spatial filters to specular reflected light along the axis of beam 12. The defects that appear on the surface 14 of UUT may be as small as 1 μm in area. A defect may extend beyond the diameter of the laser beam, namely beyond 250 μm, in which case its shape, as distinguished from its mere size, will be detected by the scanning process. Surface defects scatter a sufficient amount of light beyond prism 20 so as to be detected by photodetector 26. In general, since an ideally optically flat surface will not scatter light, the defect will have surface portions that are not optically flat with respect to the incident light.

An aperture mask 25 acts as the second spatial filter in optical system 10 and prevents ambient light from being projected onto the detector 26. The output of detector 26 is applied to an amplifier circuit 28 which provides an output signal to either or both a counter display 30 or a cathode ray tube (CRT) display 32. Counter display 30 counts the number of defects that are detected during a scan of beam 12. The CRT display 32 provides a visual display of the relative spatial distributions of the locations of the defects on the UUT. Amplifier 28 is a high gain amplifier analogue in nature and produces an amplifier output of the detector output with respect to the input signal it receives from detector 26 at terminal 28a. This results in gray scale in the CRT display 32, the intensity of the indications of defects on the CRT screen being indicative of the defects. A more detailed schematic of amplifier 28 is shown in FIG. 2 to be described.

In the form of the scanner shown in FIG. 1, the beam 12 scans the UUT in spiral fashion and the electron beam of the display 32 is also scanned in spiral fashion. The UUT may be a circular surface and for such purposes a spiral pattern is useful. For square shaped surfaces a circular inscribed portion is scanned. If desired, the pattern may be converted into an X-Y display which is achieved by the coordinate transformation system 60 which transforms polar coordinates of the beam striking at surface 14 into suitable rectangular coordinates which are applied as X-Y coordinate inputs for the display 32. A detailed description of the polar coordinate system is not given here, but a more detailed description is given of this and other features in the above-identified copending application Ser. No. 000,813, described above and incorporated by reference hereby. In brief, the coordinate system 60 includes a polarizer $P_R$, spaced, stationary analyzers $P_y$ and $P_x$, and detectors 74 and 76 excited by the light emitting photodiodes $L_x$ and $L_y$, which are energized by power supply 73. The system 60 includes a shaft 62 rotating in direction 64 over rotatable table support 42 slideable by motor 40. A gear 66 connected to shaft 62 is meshed with gear 48 so that the polarizer $P_R$ rotates at a predetermined angular speed, typically one half the angular speed of the UUT on table 44 rotated by shaft 46 in direction 38. The light from the diodes $L_x$ and $L_y$ are passed through the polarizer $P_R$ and detected by detector 74 and 76 and applied to the processing circuit 54. A wiper arm 50 is connected (dashed line 56) to the table 42 and moves with the table 42 as the table translates in the direction x'. The wiper arm 50 is part of a potentiometer 52 which is connected to processing circuit 54 for position control purposes. The processing circuit 54 provides the X and Y signals for application to the CRT 32 in the manner described in the above-identified application of Steigmeier et al.

In operation, when the incident beam 12 is positioned at the center of the UUT, the output of amplifier 28 is zero. As the beam 12 is moved from the center, signals are detected by detector 26 and applied to amplifier circuit 28 and applied to display 32. The display is scanned in an X-Y direction, providing a visual display corresponding to the scattered light from the beam 12. The display appears as bright spots and positions of the spots on the display screen correspond to the spatial distribution of the locations of the defects on or close to the surface of the UUT.

Figure 2:
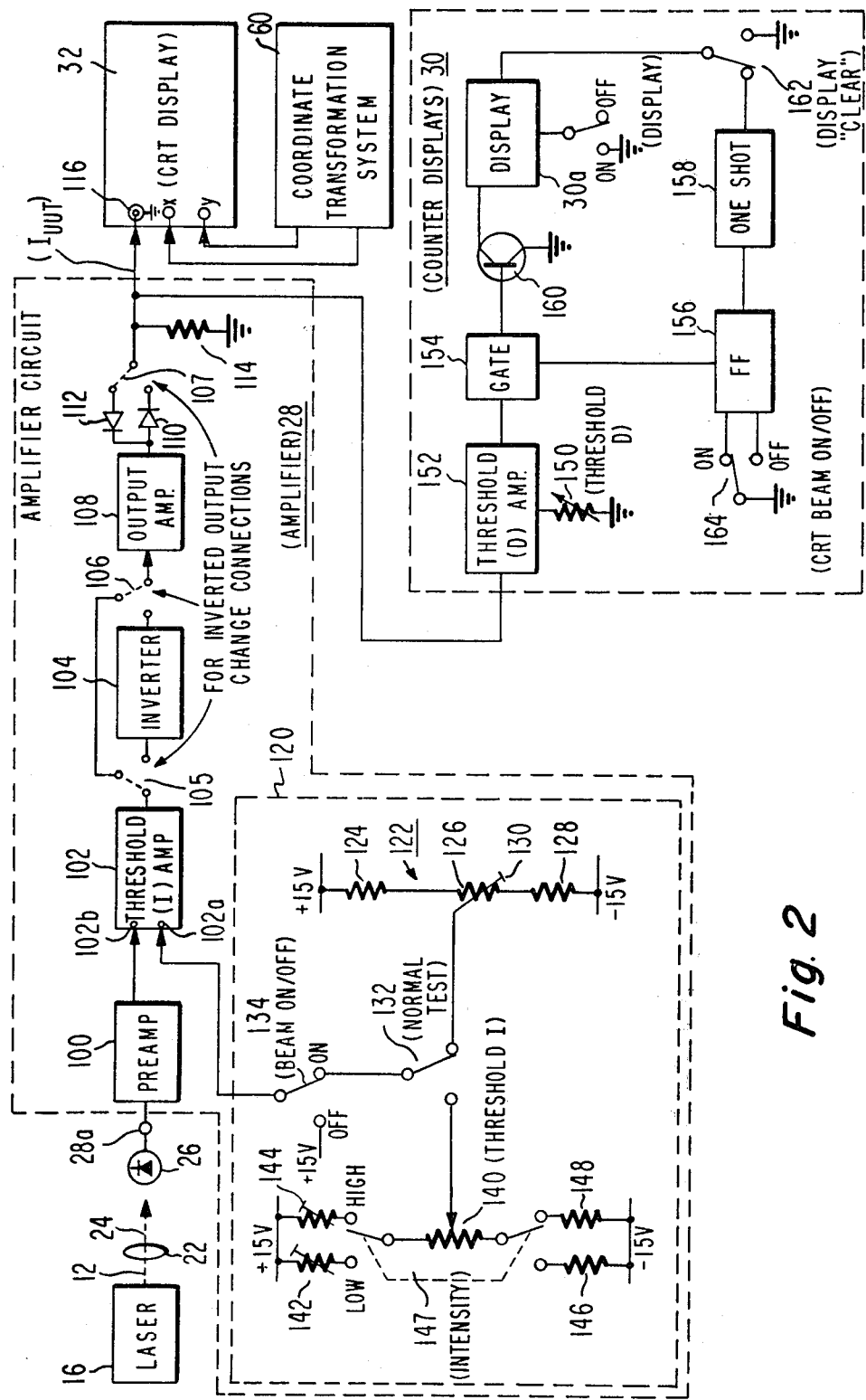
FIG. 2 is a block schematic of the amplifier circuit of the scanner illustrated in FIG. 1.

Reference is now made to FIG. 2, which shows particularly the amplifier circuit 28 in detail and its relation to other portions of the system. Laser 16 provides a fixed intensity beam 12 which is scattered as beam 24 which, in turn, is detected by detector 26. The output of detector 25 is coupled via terminal 28a to a preamplifier 100 which in turn is coupled to a threshold current amplifier 102 and thence through one way or another single pole, double throw switch or straps 105 and eventually switch 106. The threshold signal from amplifier 102 is either applied directly to an inverter 104 or, in the alternative, to an output amplifier 108. Single pole, double throw switch 107 inserts either one of diodes 110 or 112 in the circuit depending upon the insertion or removal of inverter 104 by switches 105 and 106. Inverter 104 is used, if desired, to invert the output signal of amplifier 102 whereby the display of a detected defect signal will be inverted. Output resistor 114 (connected to ground) provides the output signal which is applied to the cathode of the CRT 32, as at terminal 116.

A threshold control network 120 provides a means for controlling to a predetermined or preselected value the intensity 1 of the beam of the CRT display 32. The network 120 comprises for testing a reference potentiometer 122 formed of serial resistors 124, 126 and 128 connected between +15 volts and −15 volts. An adjustment tap 130 is connected to one terminal of a single pole, double throw switch 132, the common terminal of which is connected to another switch 134 and thence to the input 102a of "threshold amplifier" 102. This network 120 provides in a test mode an adjustable voltage to the threshold (I) amplifier 102 to provide a suitable test signal for display on the CRT display 32 for alignment amplifier testing purposes, etc. Threshold amplifier 102 is a suitable operational amplifier having a first input 102b and a second input 102a. The network 120 with the switches 132 and 134 in the position as shown provides a control voltage to terminal 102a of amplifier 102 as the test mode of operation during which the laser is scanning the UUT or wafer. In this test mode a light emitting diode 60a is triggered by the coordinate transformation system 60 to flash light pulses four times per revolution of the wafer UUT (14) at the detector 26. The output signal of detector 26 after amplification through preamplifier 100 and amplifier 102 and 108 produces a test pattern on the CRT display 32 for judging the good alignment values of the optics and the good working condition of the electronics.

For normal operation to preset the predetermined threshold at which the CRT beam provides a predetermined intensity I, a threshold intensity adjustment potentiometer 140 is connected by ganged switch 147 between either one of a pair of selectable resistors 142 and 144 connected in common to +15 volts, the other terminals being connected to switch 147 through a pair of resistors 146 and 148 to −15 volts. The resistors can be selected to provide different voltage ranges to thereby change the intensity of the CRT beam over a wide range of values as desired.

In operation, with switches 134 and 132 positioned to the "normal" position opposite to that shown in FIG. 2, the intensity threshold (I) control 140 will be in the circuit. By adjusting potentiometer 140, the intensity (I) of the CRT beam may be adjusted to a predetermined value. Suitable calibration indicia (for example, "0" to "1000" on the potentiometer are provided (not shown) as a repeatable reference of the selected position of the potentiometer 140.

In addition to the threshold (I) intensity control network 120, a second threshold (D) control 150 is provided to modify the intensity signal ($I_{UUT}$) for counting display 30. The D threshold adjustment 150 provides a reference adjustment of a threshold amplifier 152 whose output is coupled to the input of a gate 154 which in turn is triggered by flip-flop 156 responding to one shot 158. Gate 154 is coupled to transistor 160 which in turn is coupled to counter 30a of display 30 shown in FIG. 1. With contact switch 162 normally in the position shown, triggered events will be registered in the display 30 and with the switch 162 operated momentarily to the other position the display 30 is cleared to "0000." Switch 164 is a switch for controlling the CRT beam according to the switch positions as shown. The coordinate transformation system 60, described above for FIG. 1, as shown in block form is coupled to terminals X and Y of the CRT scope display 32 to provide a signal for controlling the X-Y display pattern described above.

Thus, the threshold intensity (I) potentiometer 140 and threshold (D) potentiometer 150 provide an adjustable detection sensitivity control of the scattered light for the CRT 32 display and the counter display 30, respectively. The sensitivity of detection can be further changed by increasing the gain of the preamplifier 100 and the amplifier 108 or by inserting an attenuator (not shown) between the two. The intensity of the CRT display beam is adjusted by the threshold (I) potentiometer 140 to increase the detector signal sufficiently to the level at which the CRT 32 displays the detected signal.

In operation, with a UUT in position on the table 44, the scanner provides a beam 12 which in turn results in a scattered beam 24 which will, after detection, provide a display on CRT 32. Defects that may appear will be counted in the typical prior art procedures on counter display 30 and displayed on the CRT. Thus, in the prior art operation of the scanner apparatus defects on the surface of an object of semiconductor material are detected by scanning the surface and adjusting the potentiometer 140 of the threshold (I) control (FIG. 2) at various values to provide a visual display on the CRT of display 32 or a count of defects on counter display 30 as described in detail in the aforementioned Steigmeier, et al. patent application. The particular size of a defect can be identified by calibrations of setting of the threshold (I) potentiometer 140 and/or threshold (D) potentiometer 150.

Figure 3A:
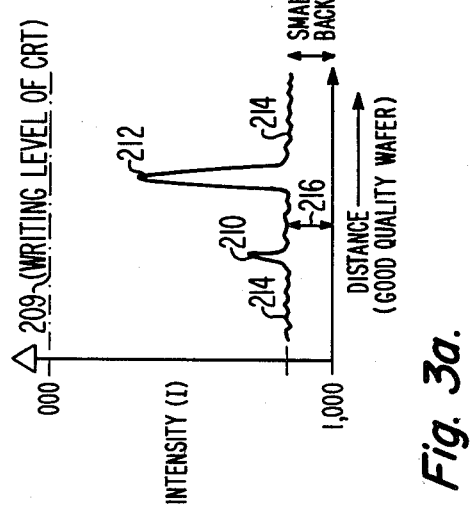
FIGS. 3a and 3b are plots, useful in understanding the invention, of the detector signals of two wafers of different quality.
Figure 3B:
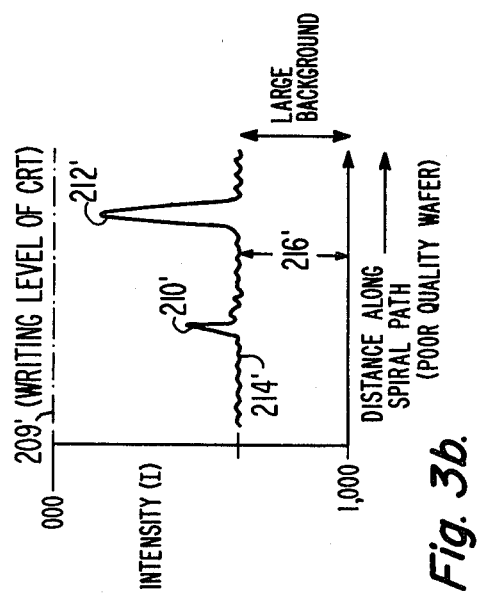

The present invention for determining the quality of the bulk material below the object surface is based on the discovery that similar identifiable defects of comparable size, appearance, density and the like on each of two different wafers but of different crystalline quality resulted from different adjustments of the threshold (I) potentiometer 140 to get what appeared to be the same defect display. It was discovered after many experiments with this observed phenomenon that a relatively good quality wafer had a significantly different threshold (I) adjustment than a relatively poor quality wafer and that such a parameter adjustment was a repetitive and reliable factor for determining at least the relative quality of the bulk or volume portion of semiconductor material. Reference is made to FIGS. 3a and 3b for a more detailed description of this phenomenon. The intensity (I) of the detected scattered signal is plotted against the distance along the spiral track path of a light scan over the wafer. With the threshold (I) potentiometer 140 set at an arbitrary value of 000 within a range of 0–1000, the display on the CRT display 32 may be represented as illustrated in FIG. 3a. The dotted-dashed lines 209 (FIG. 3a) and 209' (FIG. 3b) represent the preselected full writing level of the CRT. This level can be changed by adjustment of the CRT. The spikes 210 and 212 developed from the background response 214 represent respectively relatively small and large defects (or particulates, such as dust) on the surface of the wafer. The distance 216 represents the relative purity of quality of the bulk portion of the wafer.

Another wafer having similar defects on the surface but having bulk material beneath the surface of poorer quality than the wafer illustrated by FIG. 3a may be scanned at the same arbitrary level of "000" to produce a display such as shown in FIG. 3b. The small and large defects 210' and 212' respectively correspond to the similarly sized defects 210 and 212 ilustrated in FIG. 3a. The distance 216' represents the relative quality of the crystallinity of the bulk material of the poorer quality wafer. It is seen that the distance 216' for the wafer of FIG. 3b is significantly greater than the distance 216 for the wafer of FIG. 3a. If for both wafers the threshold I adjustment is now increased from the arbitrary value of "000", the storage scope will produce writing when the background levels 214 and 214' in FIGS. 3a and 3b, respectively, are shifted to the level of lines 209 and 209'. This occurs at the threshold I setting of 710 for the good quality wafer or at the threshold I setting of 660 for the poor quality wafer corresponding to the greater distance between the background 214 and line 209 in FIG. 3a than between background 214' and line 209' in FIG. 3b. Thus, the quality of a wafer such as that illustrated by FIG. 3b writing fully at 660 as compared to the wafer represented by FIG. 3a which is writing fully at 710 can be said to be of poorer quality.

An apparatus of the type described above for providing light scattering from the surfaces of wafers can be used to test or appraise wafers on a very rapid and accurate manner particularly useful for manufacturing of semiconductor material. The invention provides special use for semiconductor material heteroepitaxially grown on substrates such as sapphire, a procedure known in SOS IC processing but may be equally useful for homoepitaxially grown silicon.

The invention, as will now be described in detail by several examples, can be used in both a stationary and scanning mode of the apparatus of the type described in the above identified patent Steigmeier et al. application. In the practice of either mode, laser light, having a wavelength preferably in the range of wavelengths between blue and ultraviolet, is impinged on the surface of the wafer under test. The scattered light from the illuminated area is collected as described above and detected and processed. In general, the quality of materials in addition to epitaxial silicon layers for SOS wafers can be determined although the invention is preferably practiced in evaluating SOS wafers. For other materials comprising epitaxial silicon layers or silicon thin wafers or bulk wafers, the quality can be determined by having the appropriate penetration depth of the incident light be sufficient to cause the bulk or volume portion of the material to develop scattering. This is done by appropriate selection of the wavelength of light. Moreover, the method may be extended to metal layers or thin films or other light absorbing layers to within the penetration depth of the appropriately chosen light.

Figures 4A, 4B, 4C:
FIGS. 4a, 4b, 4c, respectively, are photographs of the display during the testing of the quality of SOS wafer at different threshold adjustments.

An example of the method of the invention is demonstrated by reference to FIGS. 4a, 4b, and 4c. The photographs of FIGS. 4a–4c are that of the CRT of display 32 taken for three different threshold settings of potentiometer 140 for the same SOS wafer in the scanning mode. According to the arrangement of the apparatus, a display that is dark represents relatively good quality material while the white portions of the display represents relatively bad or poor quality material. The wafer display illustrated in FIG. 4a is indicated by a portion "1" represented by a solid circle. Circle 1 is located at the center of the wafer for reference purposes. The two dotted circles aligned vertically above circle 1 represents other surface portions of the wafer, namely, portion 2 and 3 to be discussed with respect to FIGS. 4b and 4c. The wafer as seen in FIG. 4a indicates that the area 1 is at the writing level of the CRT (transition from black to white) for a value of 740 of the threshold I potentiometer setting. Note that the lower half of the wafer is rather close (just slightly better) in quality to portion 1 since it is close to the CRT writing level for the same threshold I setting of 740.

The display illustrated by FIG. 4b was taken when the potentiometer setting is 720. It will be seen that the area portion 2 is at the writing level of the CRT for a value of the threshold I setting of 720. This is indicative of a worse quality of portion 2 than that of portion 1.

FIG. 4c illustrates a display with the threshold potentiometer set at 700. The portion 3 is at the CRT writing level for this (700) threshold I setting. Portion 3 is, therefore, the worst in quality of the three portions 1, 2 and 3 on the wafer.

Thus, the intensity of detected scattered light is a relative parameter depending on the quality of a material. This knowledge is useful in accepting or categorizing wafers to meet certain manufacturing criteria.

Figure 5A:
FIGS. 5a and 5b are photographs illustrating the use of the invention to determine a relative good quality and bad quality SOS wafer for production line use.
Figure 5B:
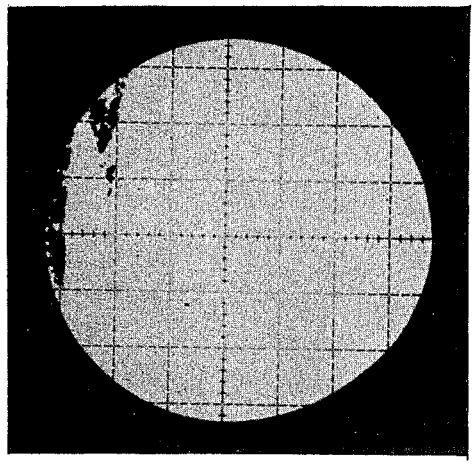

Reference is now made to FIGS. 5a and 5b providing a further illustration of how the scanning method for appraising the quality of semiconductor wafers might be used. The apparatus is set up with a preselected position of the threshold (I) potentiometer 140 set at 710. The value 710 corresponds to a setting that was determined by experiment as being the threshold of acceptability or conversely the threshold of rejection of wafers. An ultraviolet HeCd laser (3,250 angstroms) was used. The quality of many wafers were tested and appraised and found at this setting of I to have been of good quality when the display was substantially dark and poor quality wafers when the display was substantially white. Various surface portions of the wafer could be considered as being within or without a reject criterion. For example, if a wafer was of a poor quality in the peripheral portions and good quality in the central portions, the wafer could be accepted. Other conditions of acceptability can be established according to the criterion set forth by the user. (Compare, for example, FIG. 4a to FIG. 4c.)

FIG. 5a, which is a display of a good quality SOS wafer, is substantially black. FIG. 5b represents a poor quality wafer which provides a display of the scattered light signal that is substantially white. Accordingly, the wafer illustrated in FIG. 5a would be clearly acceptable whereas the wafer described in FIG. 5b would be rejected.

Figure 6:
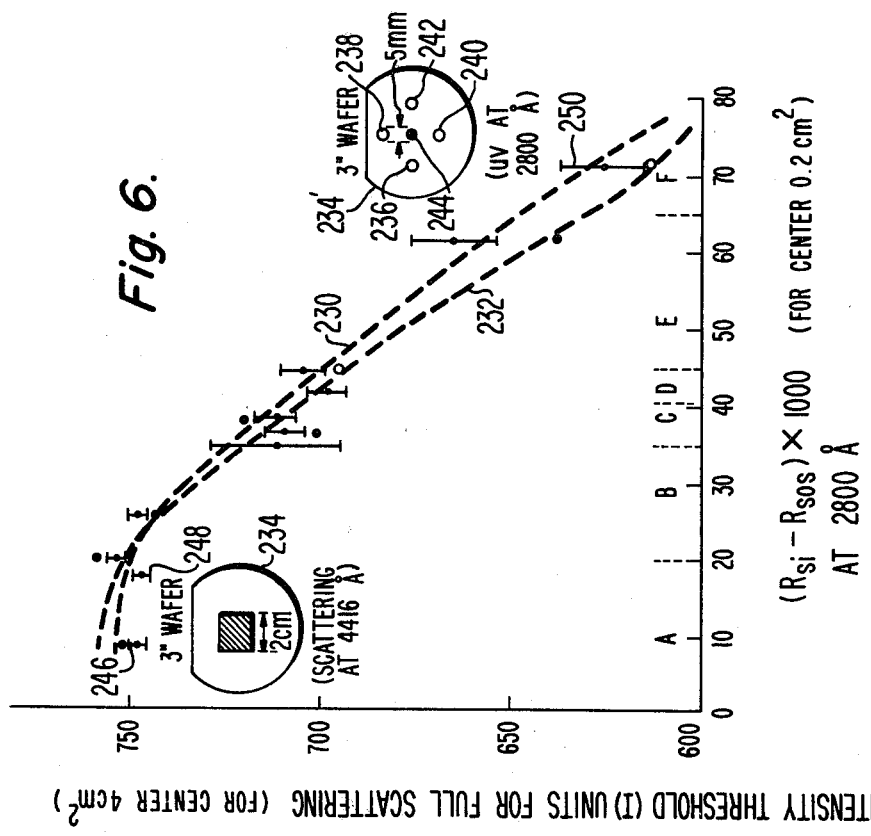
FIG. 6 is a plot showing the correlation between light scattering apparatus and ultraviolet reflection apparatus results.

During the course of tests on many wafers of varying quality, a comparison was made between the results obtained by the ultraviolet reflection techniques described in the above identified patent applications of Duffy et al. and tests made on the light scattering apparatus illustrated in FIGS. 1 and 2, respectively on the same wafers. Reference is made to FIG. 6 which is a plot of a correlation made between the tests of the same wafers by light scattering techniques of the present invention and the ultraviolet reflection techniques in the above-identified Duffy patent applications. The resulting scattering values as represented by the threshold potentiometer 140 settings are indicated on the ordinate of FIG. 6 within the range of 600–750. The abscissa represents the quality of wafers based on the ultraviolet reflection technique as described in the above-identified Duffy et al. applications, determined by the difference of the SOS wafer reflectivity ($R_{SOS}$) from the bulk silicon reflectivity ($R_{Si}$). This difference of the two measurements multiplied by 1,000 provides a relative number (10–80) as plotted along the abscissa. The measurements in this series of tests was done for light at both 4,416 angstroms as represented by curve 230 while a similar set of tests were made with an ultraviolet light laser at 3,250 angstroms represented by curve 232. The wafers tested using the light scattering techniques are illustrated by a typical wafer 234. For these tests the judged portion of the wafer consisted of a square of 2 cm as indicated. The tests for the ultraviolet reflection tests were done on the same wafer as illustrated by wafer 234'. In this instance the UV reflection was made at 5 discrete portions of the wafer represented by portions 236, 238, 240, 242 and 244 of which the portion 244 was selected for the plot of FIG. 6. The UV light was not scanned. The size of the portions exposed to the ultraviolet beam was 5 mm. The vertical bars 246, 248, etc., through 250 represent test data of the maxima, minima and average values of threshold I settings respectively for a particular wafer tested using the light scattering method of the invention, taking into account the variations over the square 234 of the wafer. The plots show very good correlation between the quality of wafers between respective techniques. Arbitrarily, the wafers were grouped as categories A to F as indicated at the lower portion of FIG. 6. The best quality wafers A are seen to include the portion of the curves 230 and 232 that are near or about the threshold setting 750. The poorer quality wafers correspond to category F in which the settings of the threshold adjustments were in the range of 625. Intermediate quality categories B, C, D, and E are clearly seen from the plot.

The invention can be practiced in the stationary mode by mainly positioning the beam 12 on the wafer by rotating the table by hand. In practice, the apparatus shown in FIG. 1 would be modified to use a simple table at the place of the UUT on which the wafer can be placed. Alternatively, a simple stage may be provided which is arranged to select five representative locations, such as those illustrated by wafer 234' in FIG. 6, on which tests could be made successively. This would provide a simpler and faster technique than scanning the entire surface and would provide a simpler technique for making an easier evaluation of the wafer on the selected spots. However, the overall quality of the wafer would be unknown in fact.

While any form of laser light may be used in the practice of the invention (e.g., light within wavelengths of 2,600–5,200 angstroms), it has been discovered that epitaxial layers of SOS wafers are somewhat transparent to blue laser light. As a result, some interference stripes have been observed in the areas that are close to but not at the threshold value of potentiometer 140 to develop a full display of the type described with respect to FIGS. 4a, 4b and 4c. In the preferred form of practicing the invention, an ultraviolet laser light is used. An ultraviolet laser light has been discovered to virtually eliminate the undesirable stripes found in the use of blue laser light.

What is claimed is:

1. The method for determining the quality of a material having a property of absorbing light to a given penetration depth comprising the steps of:
   (a) exposing one or more regions of said material to a beam of light of a selected wavelength;
   (b) detecting scattered light having an intensity greater than a threshold intensity from the exposed material to provide an electrical signal proportional to the intensity of detected scattered light above said threshold intensity;
   (c) applying the electrical signal to a visual display device to control the intensity of a display beam of the device; and
   (d) varying said threshold intensity to thereby vary the intensity of the display beam so as to provide the minimum intensity of display beam which yields a full display of the exposed material, wherein the value of the threshold intensity is a direct measure of the crystalline quality of the material.

2. The method of claim 1, wherein the light exposing step comprises scanning the light beam so as to be incident on a selected surface portion of the material.

3. The method according to claim 1, wherein the light exposing step comprises exposing the material to a plurality of selected spatially separated beams incident on the suface of the material.

4. The method according to claim 1, wherein the wavelength of said light is selected from a wavelength within the range of 2,600–5,200 angstroms.

5. The method according to claim 4, wherein said wavelength of light is 4,416 angstroms.

6. The method according to claim 5, wherein said wavelength of light is 3,250 angstroms.

7. The method according to claim 1, wherein said material comprises a layer of silicon on a substrate of sapphire.

8. The method according to claim 1, wherein said material comprises a wafer of bulk silicon material.

9. The method according to claim 1, wherein said material comprises a metal layer having an absorption characteristic to allow for a preselected penetration depth of said light.

10. The method according to claim 1, wherein said material comprises a thin layer of epitaxially grown silicon on a substrate of silicon.

11. The method according to claim 1, wherein said material comprises a dielectric.

12. The method according to claim 1, wherein said material comprises amorphous silicon.

* * * * *